US009675323B2

(12) United States Patent
McKinnis et al.

(10) Patent No.: US 9,675,323 B2
(45) Date of Patent: Jun. 13, 2017

(54) INTERNAL ULTRASOUND ASSEMBLY WITH PORT FOR FLUID INJECTION

(71) Applicant: Muffin Incorporated, West Lafayette, IN (US)

(72) Inventors: Peter S. McKinnis, West Lafayette, IN (US); Yun Zhou, West Lafayette, IN (US); Sarah Robbins, Lafayette, IN (US); Neal E. Fearnot, West Lafayette, IN (US)

(73) Assignee: Muffin Incorporated, West Lafayette, IN (US)

( * ) Notice: Subject to any disclaimer, the term of this patent is extended or adjusted under 35 U.S.C. 154(b) by 449 days.

(21) Appl. No.: 14/211,780

(22) Filed: Mar. 14, 2014

(65) Prior Publication Data

US 2014/0276083 A1    Sep. 18, 2014

Related U.S. Application Data

(60) Provisional application No. 61/787,768, filed on Mar. 15, 2013.

(51) Int. Cl.
*A61B 8/00* (2006.01)
*A61B 8/12* (2006.01)
(Continued)

(52) U.S. Cl.
CPC ............ *A61B 8/4281* (2013.01); *A61B 8/12* (2013.01); *A61B 8/4272* (2013.01); *A61B 8/445* (2013.01);
(Continued)

(58) Field of Classification Search
CPC ............................ A61B 1/00064; A61B 8/445
See application file for complete search history.

(56) References Cited

U.S. PATENT DOCUMENTS 2,790,095 A    4/1957   Peek et al.
4,421,118 A   12/1983   Dow et al.
(Continued)

FOREIGN PATENT DOCUMENTS

JP    06-209939 A    8/1994
JP    1994-209929 A * 8/1994 ............... A61B 8/12
(Continued)

OTHER PUBLICATIONS

International Search Report and Written Opinion issued in PCT/US2013/064570, dated Jan. 24, 2014.
(Continued)

*Primary Examiner* — Katherine Fernandez
*Assistant Examiner* — Michael Kellogg

(57) ABSTRACT

There are disclosed embodiments of devices and methods for imaging the inside of a body part, particularly a blood vessel. In particular embodiments, a catheter has a tip chamber, within which is an ultrasound transducer mounted on a pivot mechanism, a motor for turning the transducer, and an implement for pivoting the transducer. Examples of such an implement are a linear motor, a shaft or filament, and the pivot mechanism may be biased to return to a base position when the implement is not pivoting the transducer. In other embodiments, a mirror reflecting ultrasound signals from the transducer may be rotated and/or pivoted, using similar mechanisms.

39 Claims, 3 Drawing Sheets

(51) Int. Cl.
  *A61B 1/00* (2006.01)
  *A61B 8/08* (2006.01)
  *A61N 7/02* (2006.01)
  *A61N 7/00* (2006.01)

(52) U.S. Cl.
  CPC ........ *A61B 8/4461* (2013.01); *A61B 1/00064* (2013.01); *A61B 8/0891* (2013.01); *A61N 7/022* (2013.01); *A61N 2007/0043* (2013.01); *A61N 2007/0082* (2013.01)

(56) References Cited

U.S. PATENT DOCUMENTS

| | | |
|---|---|---|
| 4,785,816 A | 11/1988 | Dow et al. |
| 5,237,884 A | 8/1993 | Seto |
| 5,373,845 A | 12/1994 | Gardineer et al. |
| 5,437,283 A | 8/1995 | Ranalletta et al. |
| 5,535,715 A | 7/1996 | Mouton |
| 5,611,246 A | 3/1997 | Long et al. |
| 6,248,074 B1 | 6/2001 | Ohno et al. |
| 6,354,814 B1 | 3/2002 | Kaufmann et al. |
| 6,371,915 B1 | 4/2002 | Koger et al. |
| 7,798,971 B2 | 9/2010 | Flesch et al. |
| 8,206,307 B2 | 6/2012 | Barnard et al. |
| 8,214,010 B2 | 7/2012 | Courtney et al. |
| 2002/0082503 A1 | 6/2002 | Chandrasekaran et al. |
| 2002/0087083 A1 | 7/2002 | Nix et al. |
| 2002/0143252 A1 | 10/2002 | Dunne et al. |
| 2005/0203416 A1 | 9/2005 | Angelsen et al. |
| 2006/0030797 A1 | 2/2006 | Zhou et al. |
| 2006/0173348 A1 | 8/2006 | Wilser et al. |
| 2007/0038114 A1 | 2/2007 | Couvillon, Jr. |
| 2007/0149917 A1 | 6/2007 | Bennett et al. |
| 2007/0167813 A1 * | 7/2007 | Lee .................. A61B 8/12 600/459 |
| 2007/0167821 A1 | 7/2007 | Lee et al. |
| 2008/0097403 A1 | 4/2008 | Donaldson et al. |
| 2008/0177138 A1 | 7/2008 | Courtney et al. |
| 2008/0221506 A1 | 9/2008 | Rodriguez et al. |
| 2008/0234716 A1 | 9/2008 | Kiester |
| 2008/0312536 A1 * | 12/2008 | Dala-Krishna ......... A61B 8/12 600/459 |
| 2009/0088631 A1 | 4/2009 | Dietz et al. |
| 2009/0306518 A1 | 12/2009 | Kurse et al. |
| 2010/0036258 A1 | 2/2010 | Dietz et al. |
| 2010/0145310 A1 | 6/2010 | Lee et al. |
| 2010/0160788 A1 | 6/2010 | Davies et al. |
| 2010/0179426 A1 | 7/2010 | Davies et al. |
| 2010/0234736 A1 | 9/2010 | Corl |
| 2010/0249601 A1 | 9/2010 | Courtney |
| 2010/0249602 A1 | 9/2010 | Buckley et al. |
| 2010/0249604 A1 | 9/2010 | Hastings et al. |
| 2011/0021924 A1 | 1/2011 | Sethuraman et al. |
| 2011/0071401 A1 | 3/2011 | Hastings et al. |
| 2011/0196286 A1 | 8/2011 | Robertson et al. |
| 2011/0237955 A1 | 9/2011 | Dietz et al. |
| 2011/0263986 A1 | 10/2011 | Park et al. |
| 2011/0301508 A1 | 12/2011 | Sethuraman et al. |
| 2012/0108980 A1 | 5/2012 | Shilling et al. |
| 2012/0172698 A1 | 7/2012 | Teo et al. |

FOREIGN PATENT DOCUMENTS

| | | | |
|---|---|---|---|
| JP | 10-262974 A | 10/1998 | |
| JP | 1998-262974 A * | 10/1998 | ............... A61B 8/12 |
| JP | 2000-126184 A | 5/2000 | |
| JP | 2001-046375 A * | 2/2001 | ............... A61B 8/12 |
| JP | 2004/129697 | 4/2004 | |
| JP | 2007-267998 A | 10/2007 | |
| WO | WO 2012/061643 A1 | 5/2012 | |

OTHER PUBLICATIONS

International Search Report and Written Opinion issued in PCT/US2013/064579, dated Jan. 23, 2014.
International Search Report and Written Opinion issued in PCT/US2013/064606, mailed Jan. 8, 2014.
International Search Report and Written Opinion issued in PCT/US2013/064611, dated Jan. 28, 2014.
International Search Report and Written Opinion issued in PCT/US2013/064618, dated Jan. 24, 2014.
International Search Report and Written Opinion issued in PCT/US2013/078245, dated Apr. 25, 2014.
International Search Report and Written Opinion issued in PCT/US2014/023088, dated Aug. 18, 2014, 14 pgs.
International Search Report and Written Opinion issued in PCT/US2014/023092, dated Aug. 12, 2014, 16 pgs.

* cited by examiner

INTERNAL ULTRASOUND ASSEMBLY WITH PORT FOR FLUID INJECTION

This application claims the benefit of U.S. Provisional Application Ser. No. 61/787,768, filed on Mar. 15, 2013, which is incorporated herein by reference in its entirety.

The present disclosure relates to structure and methods in medical uses of ultrasound. In particular, this disclosure relates to preparation of medical ultrasound devices.

BACKGROUND

In using ultrasound for imaging, therapy or other medical uses, ultrasound energy or waves are transmitted through a medium and can reflect, scatter or otherwise attenuate when they reach a surface or border having a significant difference in acoustic impedance. For example, in ultrasound imaging of the human body, ultrasound waves may be applied externally (e.g. by placing a transducer on the skin) or internally (e.g. by placing a transducer within a vessel or organ), and travel through the body's internal fluids, which is a large proportion of water. When the waves strike a bone, organ or other body portion that provides an acoustic interface—i.e., a border of two significantly different acoustic impedances—then the waves are reflected or otherwise attenuated. A transducer (which may be the same transducer that supplied the ultrasound waves or another) receives the reflected or attenuated waves, and an image of a portion of the body can be generated.

An external transducer is placed against the skin with a gel useful as a coupling medium so that little or no reflection or other attenuation from the boundary between the air over the patient and the skin occurs. When a transducer is placed within the body, commonly it is inside a protective envelope, such as a tube, catheter or similar housing or enclosure. The material of such an envelope may be selected for its similarity in acoustic impedance to that of bodily fluids, so that there is little or no attenuation as ultrasound waves travel from that material to the fluids or tissues of the body. The inner pocket or volume of the body within which the transducer is placed needs a coupling medium having an acoustic impedance similar to that of the envelope material and the body's fluids, to allow maximum transmission. Without such a medium, e.g. if the inside of the body simply includes air or another gas, significant reflection or other attenuation will occur when the ultrasound energy from the transducer hits the boundary where the gas meets the material of the envelope. Suitable coupling media include biocompatible fluids such as saline, oils such as mineral oil or castor oil, alcohols, and other fluids.

Of course, some coupling media (e.g. saline) can be corrosive over time, particularly of metallic materials. If a corrosive coupling medium is to be used, a drawback is that degradation of part(s) of the transducer or other aspects of the device (e.g. structure used to turn or move the transducer) may occur. An unacceptably short shelf life for the product may thus result with such media. Thus, the relatively low-cost medium of saline has significant downside to a practical internal transducer product.

Embodiments of internal transducer products using piezoelectric motors to turn or otherwise move a transducer have also been suggested. Applicable piezoelectric motors generally need dry conditions to operate, as they require a high friction contact area between a stator and a clutch. If fluid touches that contact area or interface, the friction will be substantially reduced, thereby also reducing the torque output of the motor Accordingly, in such embodiments to prevent fluid from contacting the motor a seal is included between the motor and the transducer, to prevent leakage of the coupling medium from the volume around the transducer toward the motor. Such seals can fail over time, which is one potential factor in shelf life for such products.

SUMMARY

Among other things, there are shown embodiments of apparatus for ultrasound procedures that include a transducer for emitting and/or receiving ultrasound signals, the transducer being within a sealed chamber that is defined at least partially by a wall forming an acoustic window for transmission of ultrasound signals. An injection port communicates with the chamber through which coupling media is inserted into the chamber, and an exhaust port communicates with the chamber through which gas within the chamber is exhausted from the chamber when coupling media is inserted into the chamber.

In particular examples, the injection port includes a flexible insert fixed with respect to the wall, the insert permitting insertion of a needle through it and thereafter providing an airtight seal when a needle is removed from it. Such an insert may be placed at a forward-most tip of the chamber. In other examples, the chamber is attached to or part of an elongated tubular housing having an internal surface and an external surface, and the injection port includes a lumen opening into the chamber and extending through at least part of the housing between the internal surface and the external surface. At least part of the lumen may be within a tube separate from the housing. The lumen can open into the chamber at a rearward-most portion of the chamber.

Embodiments are disclosed in which the exhaust port includes a valve fixed with respect to the wall. The valve may be placed in the wall at a rearward-most portion of the chamber. Other embodiments may have the chamber attached to or part of an elongated tubular housing having an internal surface and an external surface, with the exhaust port including a lumen opening into the chamber and extending through at least part of the housing between the internal surface and the external surface. For example, at least part of the lumen may be within a tube separate from the housing. The lumen can open into the chamber at a rearward-most portion of the chamber.

Such devices can include a motor (one or more) operatively connected to the transducer, and a seal between the motor and the transducer and fixed to the wall, the seal defining a rearward boundary of the chamber. Particular examples have the injection port located opposite and facing the seal. Other examples have one or both of the injection port and exhaust port located adjacent the seal. Embodiments in which the injection port and the exhaust port are located diametrically opposed from each other are also shown.

Methods for preparing and using devices for ultrasound procedures are also disclosed. For example, such methods can include injecting a coupling media into a sealed chamber, the chamber defined at least partially by a wall forming an acoustic window for transmission of ultrasound signals, and the chamber having within it a transducer for emitting and/or receiving ultrasound signals. The injecting can include moving the coupling media through an injection port that communicates with the chamber, and during the injecting, gas within the chamber prior to the injecting is forced out of the chamber through an exhaust port. The injecting can continue until a sufficient amount of coupling medium is injected, e.g. the coupling medium displaces substantially all of the gas. Particular examples of the injecting include inserting a needle through the injection port and passing the coupling medium through the needle and into the chamber. Other examples of the injecting include passing the coupling medium through a lumen in a tube, at least part of the tube being within a housing of the device. In embodiments in which the exhaust port includes a valve, during the injecting gas within the chamber prior to the injecting may be forced out of the chamber and exterior of the device through the valve. Where the exhaust port includes a lumen in a tube, at least part of the tube being within a housing of the device, during the injecting gas within the chamber prior to the injecting may be forced out of the chamber through at least part of the lumen.

These and other embodiments are discussed further below.

DETAILED DESCRIPTION OF THE ILLUSTRATED EMBODIMENTS

Figure 1:
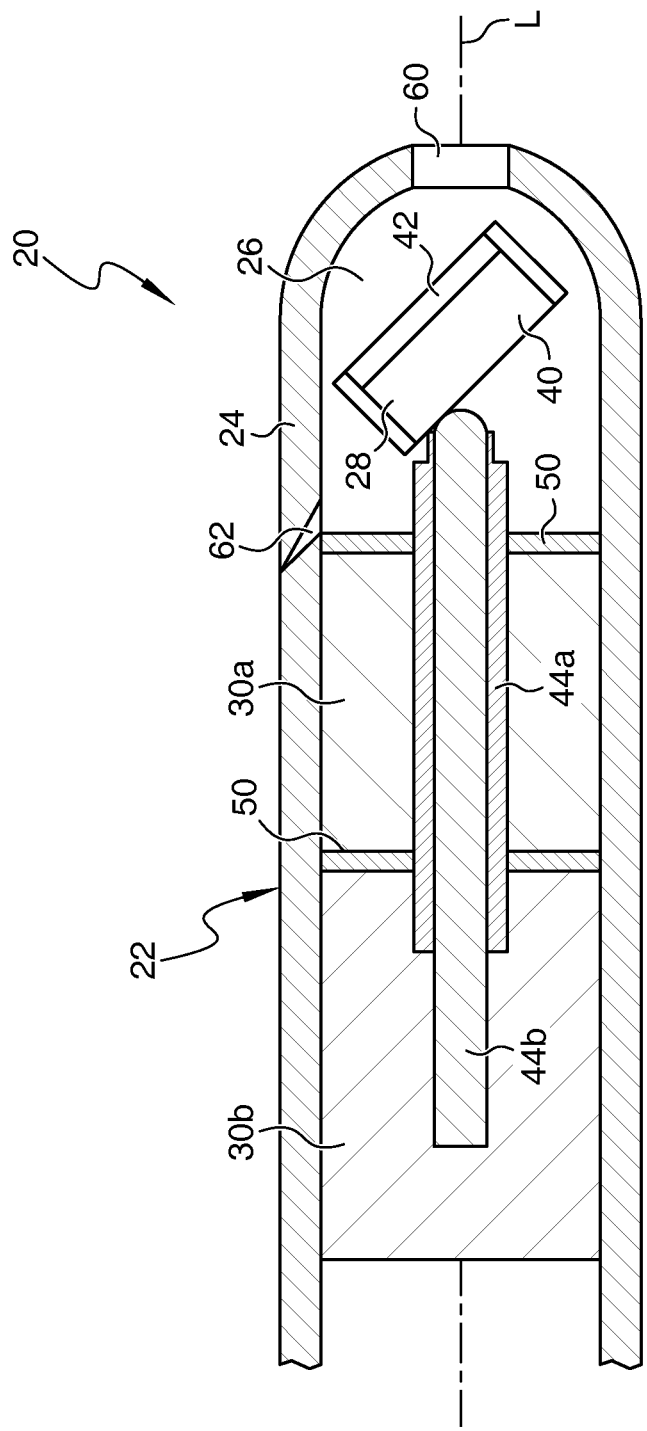
FIG. 1 is a part cross-sectional view of an embodiment of a device for use in ultrasound procedures.

For the purposes of promoting an understanding of the principles of the disclosure, reference will now be made to the embodiments illustrated in the drawings and specific language will be used to describe the same. It will nevertheless be understood that no limitation of the scope of the claims is thereby intended, such alterations and further modifications in the illustrated embodiments, and such further applications of the principles of the disclosure as illustrated therein being contemplated as would normally occur to one skilled in the art to which the disclosure relates.

Referring now generally to the drawings, there is shown an embodiment of a device 20 for application of ultrasound internally to a patient. As particular examples, device 20 is or is part of a device or system for imaging, such as for intravascular ultrasound (IVUS) imaging. Other embodiments can include devices for therapeutic or diagnostic uses within the body, or for ultrasound devices used outside of the body. In the embodiment indicated schematically in FIG. 1, device 20 is a catheter or other flexible elongated or tubular housing or member 22 having an application end with a wall 24 defining an internal chamber 26, with catheter 22 being sized and configured in a particular example for insertion into and/or travel along the vascular system. Within catheter 22 and chamber 26 in this embodiment is a transducer 28 for sending and/or receiving ultrasound signals. In particular embodiments, one motor 30 may be provided, connected directly or indirectly to transducer 28 so as to turn transducer 28 around a longitudinal axis of device 20, pivot transducer 28 around an axis substantially perpendicular to that longitudinal axis, and/or provide other motions to transducer 28. As discussed further below, one or more motors 30 (e.g. two motors 30a and 30b indicated in the illustrated embodiments) may be provided within catheter or housing 22 and are connected directly or indirectly to transducer 28 so as to turn transducer 28 around a longitudinal axis of device 20, pivot transducer 28 around an axis substantially perpendicular to that longitudinal axis, and/or provide other motions to transducer 28.

Catheter 22 in the illustrated embodiment is an elongated device of plastic or other sturdy flexible material that is substantially transparent to or presenting a minimal barrier to passage of ultrasound signals. For example, when used within a blood vessel containing body tissues and blood, it is preferable for catheter 22 (or at least some or all of wall 24) to be constructed of a material which has an acoustic impedance similar to that of body fluids such as blood. Possible materials could include, for example, a polymer material such as high density polyethylene (HDPE), polymethylpentene (PMP), or acrylonitrile butadiene styrene (ABS). It has been determined that a preferred thickness of at least the portion of catheter 22 which serves as the viewing window is approximately ½ of the wavelength corresponding to center frequency.

Wall 24 surrounds chamber 26, which is at the distal end of device 20 in the illustrated embodiment, and extends proximally. Wall 24 is a monolithic part of a catheter 22 in some embodiments, and in others wall 24 is at the application end surrounding all or part of chamber 26. Wall 24 may extend toward the control end of device 20 beyond chamber 26 in some examples. The proximal end of wall 24 and/or catheter 22 may extend outside of the patient during use, and the control end may include a handle or other operating portion (e.g. an imaging system and/or a maneuvering system (not shown)). Particular embodiments of catheter 22 or at least chamber 26 are cylindrical, and are sized for insertion into and passage through blood vessels, such as insertion into the femoral artery and passage through it toward the heart.

Transducer 28 is indicated schematically in the drawings. The term "transducer" should be understood to include an assembly of two or more parts as well as a single piece. For instance, transducer 28 can include a body or backing 40 with a transducer element 42 attached to one side of body 40, and a matching layer (not shown) attached to one side of element 42. The matching layer is attached to one side of element 42 and may be focused or non-focused. The matching layer has acoustic impedance generally between that of element 42 and the medium surrounding transducer 28 in order to minimize mismatched acoustic impedance between transducer 28 and the medium surrounding transducer 28 (e.g. mineral oil). In some embodiments, transducer 28 includes an element 42 and matching layer but no body 40. In this embodiment, transducer 28 is pivotable and/or rotatable through action or influence of motor 30, so that with element 42 on the side of body 40 as indicated, a generally lateral (i.e. away from the longitudinal axis) and forward ultrasound beam direction is possible depending on the motion of transducer 28. Embodiments of transducer 28 may be capable in particular examples of sending and receiving ultrasound waves in a range of frequencies which are typically used in medical ultrasound procedures, such as, for example, in the range from 2 MHz to 50 MHz.

Transducer 28 is electronically connected to a power source and to an imaging system (not shown). Examples of connections include conductors (e.g. wires or cables) along wall 24, through a central lumen of a motor shaft, via slip ring connections, and/or via metallic film(s) along wall 24. Transducer 28 may be mounted in a pivoting mechanism or otherwise linked to motor 30 or a shaft 44 (which rotates, travels longitudinally, or otherwise moves) to permit transducer 28 to turn, pivot, or otherwise move. Embodiments of such examples are discussed and shown in Application Ser. Nos. 61/713,135; 61/713,172; 61/714,275; and 61/748,773, all of which are incorporated by reference in their entireties.

Motor 30 may be a rotary or linear motor and includes a shaft 44 for connecting or linking to transducer 28 or a mechanism connected to it. In the illustrated embodiments, a rotary motor 30a and a linear motor 30b are provided, with respective shafts 44a and 44b. Motor 30a turns hollow shaft 44a about a longitudinal axis L of device 20, and shaft 44a is linked to transducer 28 as schematically indicated so that transducer 28 likewise turns around axis L. Motor 30b moves shaft 44b forward and backward along axis L and through shaft 44a in this example, with shaft 44b engaging or linked (not visible in FIG. 1) to transducer 28 off-center. Forward motion of 44b tends to pivot transducer 28 clockwise about an axis into the page (perpendicular to axis L), and rearward motion of shaft 44b tends to pivot or allow pivoting of transducer 28 counterclockwise around an axis into the page.

Embodiments of piezoelectric or electromagnetic micromotors of a size and configuration suitable for containment within catheter 22 may be used. For example, a particular embodiment of a rotary motor (e.g. motor 30a) is a two-phase, coreless, brushless DC electromagnetic motor, which has few components, small size and minimal complexity. A piezoelectric micromotor is of a small size, such as having a diameter in the range from 0.3 mm to 4 mm in particular embodiments, and can exhibit a high torque-to-size ratio. An example of a linear motor (e.g. motor 30b) is an electromagnetic motor similar to a voice coil, used extensively for loudspeakers, which operate by creating a high static magnetic flux (e.g. by a permanent magnet) in the lateral direction (e.g. perpendicular to the longitudinal axis of the motor). An electrically conductive coil is placed through this flux and when current is applied to the coil a force in the axial direction is created, pulling or pushing shaft 44b.

One or more seals 50 may be provided. For example, respective seal(s) 50 are provided in this embodiment forward of motor(s) 30 (e.g. engaging or adjacent to the forward-most part of each of motors 30a and 30b in the illustrated embodiment) to separate chamber 26 from motor 30. Seal 50 in the illustrated embodiment is a wall or membrane that extends across the entire diameter or width of the space within wall 24, e.g. chamber 26. Seal 50 may be unitary, formed with wall 24 and of the same material as wall 24, or may be separately formed and inserted into and joined with the inside of wall 24. As indicated in the drawings, one or more shafts (e.g. shafts 44a and/or 44b, associated with motors 30a and/or 30b) extend through seal 50 in order to link or connect to transducer 28. In such embodiments, a seal 50 thus provides not only a general wall bounding chamber 26, but seal(s) 50 also inhibit or prevent flow of fluid out of chamber 26 and/or around shaft(s) 44 extending through seal(s) 50. Particular configurations and examples of seals are shown in Application Ser. No. 61/787,357, entitled "Internal Ultrasound Assembly Fluid Seal" and filed on Mar. 15, 2013, which is incorporated herein by reference in its entirety.

Figure 2:
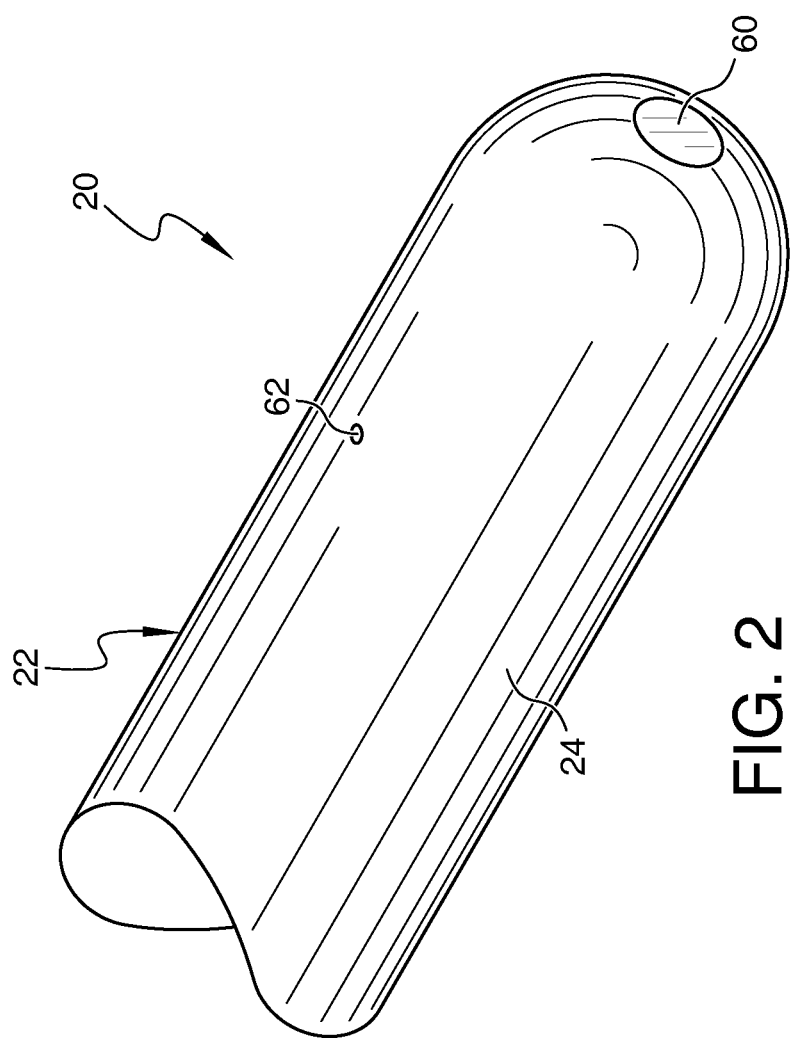
FIG. 2 is a partial perspective view of the embodiment of FIG. 1.

Wall 24 in the illustrated embodiments includes features to permit easy and effective injection of a coupling medium into chamber 26. In the embodiment shown in FIGS. 1-2, an injection port 60 is provided in a portion of wall 24, as is an exhaust port 62. Injection port 60 in this embodiment is an insert sealingly fitted into wall 24, i.e. the insert is fitted in wall 24 so that any border between them is at least substantially leak-tight. The insert in particular embodiments has self-sealing properties. In other embodiments, injection port 60 may be formed in or along with wall 24, or if wall 24 is made of a suitable material, injection port 60 may simply be a portion (or any portion) of wall 24 surrounding chamber 26. The material of injection port 60 in particular examples is a natural or synthetic rubber or rubber-like material, which is easily pierced by a thin needle and which, when the needle is removed, resiliently closes or collapses the hole made by the needle so as to provide a leak-tight seal. Other materials may be used, beyond those that can be pierced by a needle and self-seal. The example of port 60 as shown is substantially disc-shaped and is fixed in wall 24. In particular embodiments, port 60 is at least substantially immobile in rotation and/or in translation with respect to wall 24 once placed. Turning or removing such a port may have deleterious effects on the surrounding wall 24 or other parts of device 20.

Injection port 60 is shown in the illustrated example at the forward-most point (i.e. the insertion end) of device 20. Such placement has the advantage, in devices in which transducer 20 is both rotatable around axis L and pivotable around an axis perpendicular to axis L, of locating injection port 60 in an area of lesser or least interference with visualization or other application of ultrasound waves from transducer 28. Placement of injection port 60 in a side portion of wall 24 (lateral of axis L) would locate it more directly in the sweep path of ultrasound energy traveling to and/or from transducer 28, generating a side blind spot. Thus, in particular embodiments injection port 60 is at a location not faced by the transducer, where such location is possible.

Exhaust port 62 in this embodiment is a valve fitted or placed in wall 24 in fluid communication with chamber 26. As with injection port 60, exhaust port 62 may be an insert (e.g. a valve) sealingly fitted into wall 24, i.e. the valve or other insert is fitted in wall 24 so that any border between them is at least substantially leak-tight. In other embodiments, exhaust port 62 may be formed in or along with wall 24 (e.g. a conical or otherwise narrowing passage through wall 24, having its narrowest point at the exterior of wall 24). In such an embodiment, a valve may also be placed in or along the passage, such as at or adjacent the location where port 62 meets chamber 26, or at or adjacent the location where port 62 meets the exterior of wall 24. Exhaust port 62 preferably allows gas to move from chamber 26 through port 62 to the outside of device 20 during filling or charging of chamber 26 with coupling medium, but to seal against entrance of gases or liquids from the outside into chamber 26. Exhaust port 62 is shown in the illustrated example at a rearward-most point of chamber 26, i.e. adjacent to seal 50, and in this embodiment substantially opposite to the placement of injection port 60. As with the placement of injection port 60, such placement locates exhaust port 62 in an area of lesser or least interference with visualization or other application of ultrasound waves from transducer 28, avoiding a side blind spot toward the middle of the acoustic window of wall 24 around chamber 26. In particular embodiments, exhaust port 62 is at a location not faced by the transducer, where such location is possible. It will also be noted that in embodiments in which motor(s) 30 are electromagnetic motors and the coupling medium chosen does not adversely affect such a motor, exhaust port 62 may be placed through seal 50 or in a similar location to exhaust gas and any fluid that may escape from port 62 through seal 50 and/or the motor(s). As noted previously, if any motor 30 is piezoelectric, exhaust port 62 should ensure that exhaust gas and escaping fluid is routed around or away from the motor.

In use, this embodiment of device 20 is charged or injected with a coupling medium prior to initial insertion into the body. An appropriate coupling medium is selected, such as saline, oils, alcohols or other appropriate acoustic coupling fluids. The coupling medium is loaded into a syringe with a needle (not shown) or other appropriate injection device. Using the syringe with needle as a particular example, the needle is inserted through injection port 60, so that the open tip of the needle is within chamber 26. The coupling medium is then forced through the needle and into chamber 26, as by pressing a syringe plunger. As the coupling medium enters chamber 26, it increases the pressure on the gas (e.g. air) within chamber 26. The increased pressure forces the gas out of chamber 26 through exhaust port 62. Injection of coupling medium continues until chamber 26 is filled to a satisfactory degree, for example when a maximum amount of the gas previously in chamber 26 has been replaced with coupling medium. An optimum result would be to have the entire chamber 26 filled with coupling medium, so that no visible gas pockets or bubbles are present, as gas pockets or bubbles have an acoustic impedance significantly different from the coupling medium, and thus can reflect or otherwise attenuate ultrasound waves.

It is generally desirable to limit or eliminate the opportunity for gas pockets to form within chamber 26. Accordingly, in one example, during the injecting, the user may have device 20 oriented so that exhaust port 62 points generally upward, so that it is at or near the vertically highest location of wall 24. With that orientation, coupling medium will generally pool away from exhaust port 62, naturally maintaining gas within chamber 26 between the pool of coupling medium and exhaust port 62. In another example, some or substantially all of gas within chamber 26 may be removed prior to injection of coupling medium, as by evacuating through application of vacuum directly or indirectly to port 62. Little or no gas remains to be evacuated via the pressure of the coupling medium.

Once charged with coupling medium, device 20 is inserted into the patient, for example into the patient's vascular system, and is maneuvered to the desired location. The desired therapeutic, diagnostic, imaging or other ultrasound procedure is performed, and the device can be removed. Having injected the coupling medium shortly or immediately prior to use of device 20, the chance of improper operation of device 20 due to corrosion of parts by the coupling medium or seepage through seals is minimized.

Figure 3:
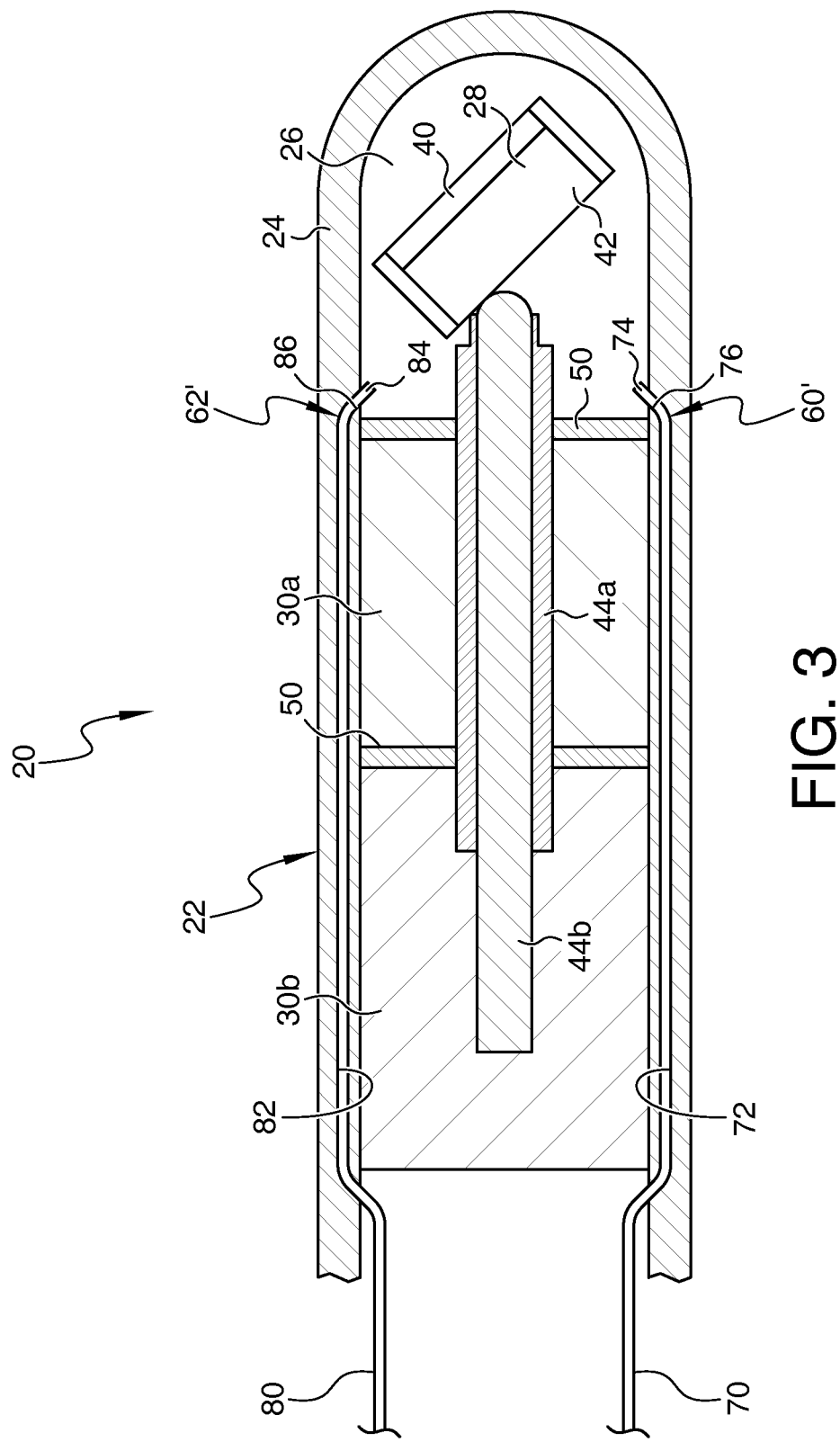
FIG. 3 is a part cross-sectional view of an embodiment of a device for use in ultrasound procedures.

In another example, indicated schematically in FIG. 3, injection port 60' and exhaust port 62', each in fluid communication with chamber 26, are shown as respective lumens traveling along at least a portion of device 20, and having respective openings in chamber 26. For instance, injection port 60' may be or include a tube 70 having a lumen 72 therethrough and a forward end opening 74 that communicates with chamber 26. In this example, a portion of tube 70 is within wall 24 around seal 50 and motor(s) 30, and tube 70 can travel within or along (e.g. fixed to) the interior surface of catheter 22 when between motor(s) 30 and the handle or operating end (not shown) of device 20. It will be understood that in other embodiments a tube 70 may extend from the handle or operating end (or from a location between the handle or operating end and motor(s) 30) to a lumen formed in wall 24, with such lumen extending through wall 24 outside of motor(s) 30 and opening into chamber 26. Further, embodiments in which tube 70 is part or all of a lumen of or within catheter 22 (e.g. a dedicated lumen of catheter 22, or a lumen extending within the wall of catheter 22 to a location at or near the operating end) are also contemplated. One or more valves 76 may be placed in or over tube 70, e.g. at the interface between tube 70 and chamber 26, to allow fluid to enter chamber 26 from tube 70 but not to escape chamber 26 into tube 70.

In a similar fashion, this embodiment of exhaust port 62' may be or include a tube 80 having a lumen 82 therethrough and a forward end opening 84 that communicates with chamber 26. In this example, a portion of tube 80 is within wall 24 around seal 50 and motor(s) 30, and tube 80 can travel within or along (e.g. fixed to) the interior surface of catheter 22 when between motor(s) 30 and the handle or operating end (not shown) of device 20. In some embodiments, a tube 80 may extend from the handle or operating end (or from a location between the handle or operating end and motor(s) 30) to a lumen 82 which extends through wall 24 outside of motor(s) 30 and opens into chamber 26, as noted above with respect to injection port 60'. Further, embodiments in which tube 80 is part or all of a lumen of or within catheter 22 (e.g. a dedicated lumen of catheter 22, or a lumen extending within the wall of catheter 22 to a location at or near the operating end) are also contemplated. As indicated in FIG. 3, a particular embodiment has injection port 60' and exhaust port 62' diametrically opposed to each other in device 20. One or more valves 86 may be placed in or over tube 80, e.g. at the interface between tube 80 and chamber 26, so as to permit exit of gas and/or liquid from chamber 26 into tube 80, and to prevent re-entry of gas or liquid into chamber 26 from tube 80.

One or both of ports 60' and 62' may be located similarly to the placement of exhaust port 62, such as at a rearward-most portion of chamber 26. Such placement locates port(s) 60' and/or 62' in an area of lesser or least interference with visualization or other application of ultrasound waves from transducer 28. In particular embodiments, one or both of injection port 60' and exhaust port 62 are at a location not faced by the transducer, where such location is possible.

Charging this embodiment of device 20 with a coupling medium can occur prior to initial insertion into the body, or at any time after device 20 is within the body. Once an appropriate coupling medium is selected, a supply of it (e.g. in a syringe (not shown) or other appropriate supply device) is connected to tube 70. In embodiments in which tube 70 extends out to a handle or operating portion (not shown) of device 20, the syringe or other supply may be connected to tube 70 in or adjacent to such operating portion. The coupling medium is forced through tube 70 and lumen 72 into chamber 26, as by pressing a syringe plunger or operating a pump. As the coupling medium enters chamber 26, it increases the pressure on the gas (e.g. air) within chamber 26. The increased pressure forces the gas out of chamber 26 through exhaust port 62', e.g. through opening 84 and into lumen 82 of tube 80. Injection of coupling medium continues until chamber 26 is filled to a satisfactory and/or optimum degree, as described above. As previously noted, as a way to help limit or eliminate the opportunity for gas pockets to form within chamber 26, during the injecting the user may have device 20 oriented (to the extent practical in a given situation) with exhaust port 62', and particularly opening 84, generally upward, so that it is at or near the vertically highest location of wall 24. With that orientation, coupling medium will generally pool away from opening 84, naturally maintaining gas within chamber 26 between the pool of coupling medium and opening. In some embodiments, gas from the chamber can be evacuated prior to insertion or injection of coupling medium, rather than by the pressure of the applied coupling medium. For example, a source of vacuum can be applied to tube 80, to withdraw gas through port 62', and then coupling medium can be added to chamber 26 via tube 70.

Once charged with coupling medium, device 20 is inserted into the patient, for example into the patient's vascular system, and is maneuvered to the desired location. The desired therapeutic, diagnostic, imaging or other ultrasound procedure is performed, and the device can be removed. Having injected the coupling medium shortly or immediately prior to use of device 20, the chance of improper operation of device 20 due to corrosion of parts by the coupling medium or seepage through seals is minimized.

The arrangement of ports 60, 62 does not require as much space in the wall or around the motor(s) 30, as is needed for the placement of tubes 70, 80 of ports 60', 62'. Such space considerations can be quite important for uses of ultrasound in small areas, such as cardiovascular (e.g. peripheral vascular) applications. As will be appreciated, ports 60', 62' provide the ability to charge chamber 26 with coupling medium in situ, rather than charging and then inserting device 20. Confirmation of the orientation of a device 20 with ports 60', 62' may be necessary if it is desired to maintain port 62' in an upward location during charging.

It will be understood that parts of the embodiments noted above can be interchanged with each other. For example, an embodiment of device 20 could include an injection port 60 and an exhaust port 62', or an embodiment of device 20 could include an injection port 60' and an exhaust port 62.

While the embodiments have been illustrated and described in detail in the drawings and foregoing description, the same is to be considered as illustrative and not restrictive in character, it being understood that only particular embodiments have been shown and described and that all changes and modifications that come within the spirit of the disclosure are desired to be protected. It will be understood that features or attributes noted with respect to one or more specific embodiments may be used or incorporated into other embodiments of the structures and methods disclosed.

What is claimed is:

1. An apparatus for ultrasound procedures, comprising:
   a transducer for emitting and/or receiving ultrasound signals, the transducer being within a chamber, the chamber defined at least partially by a wall forming an acoustic window for transmission of ultrasound signals;
   an injection port extending through the wall forming an acoustic window and communicating with the chamber adapted for passing coupling media through and into the chamber; and
   an exhaust port extending through the wall forming an acoustic window and communicating with the chamber through which gas within the chamber can be exhausted from the chamber when coupling media is inserted into the chamber, and
   wherein the chamber is attached to or part of an elongated tubular housing having an internal surface and an external surface, and wherein the injection port comprises a lumen opening into the chamber and extending through at least part of the housing between the internal surface and the external surface.

2. The apparatus of claim 1, wherein the injection port comprises a flexible insert fixed with respect to the wall, the insert permitting insertion of a needle through it and thereafter providing a leak-tight seal when the needle is removed from it.

3. The apparatus of claim 2, wherein the insert is placed at a forward-most tip of the chamber.

4. The apparatus of claim 1, wherein at least part of the lumen is within a tube separate from the housing.

5. The apparatus of claim 1, wherein the lumen opens into the chamber at a location not faced by the transducer.

6. The apparatus of claim 1, wherein the exhaust port comprises a valve fixed with respect to the wall.

7. The apparatus of claim 6, wherein the valve is placed in the wall at a location not faced by the transducer.

8. The apparatus of claim 1, further comprising a motor operatively connected to the transducer, and a seal between the motor and the transducer and fixed to the wall, the seal defining a rearward boundary of the chamber.

9. The apparatus of claim 8, wherein the injection port is located opposite and facing the seal.

10. The apparatus of claim 8, wherein the injection port is located adjacent the seal.

11. The apparatus of claim 8, wherein the exhaust port is located adjacent the seal.

12. The apparatus of claim 8, wherein the injection port and the exhaust port are located diametrically opposed from each other.

13. The apparatus of claim 1, wherein the exhaust port comprises a lumen opening into the chamber and extending through at least part of the housing between the internal surface and the external surface.

14. The apparatus of claim 13, wherein at least part of the exhaust port lumen is within a tube separate from the housing.

15. The apparatus of claim 13, wherein the exhaust port lumen opens into the chamber at a location not faced by the transducer.

16. An apparatus for ultrasound procedures, comprising:
    a transducer for emitting and/or receiving ultrasound signals, the transducer being within a chamber, the chamber defined at least partially by a wall forming an acoustic window for transmission of ultrasound signals;
    an injection port extending through the wall forming an acoustic window and communicating with the chamber adapted for passing coupling media through and into the chamber; and
    an exhaust port extending through the wall forming au acoustic window and communicating with the chamber through which gas within the chamber can be exhausted from the chamber when coupling media is inserted into the chamber, and
    wherein the chamber is attached to or part of an elongated tubular housing having an internal surface and an external surface, and wherein the exhaust port comprises a lumen opening into the chamber and extending through at least part of the housing between the internal surface and the external surface.

17. The apparatus of claim 16, wherein at least part of the lumen is within a tube separate from the housing.

18. The apparatus of claim 16, wherein the lumen opens into the chamber at a location not faced by the transducer.

19. The apparatus of claim 16, wherein the injection port comprises a flexible insert fixed with respect to the wall, the insert permitting insertion of a needle through it and thereafter providing a leak-tight seal when the needle is removed from it.

20. The apparatus of claim 19, wherein the insert is placed at a forward-most tip of the chamber.

21. The apparatus of claim 16, wherein the injection port comprises a lumen opening into the chamber and extending through at least part of the housing between the internal surface and the external surface.

22. The apparatus of claim 21, wherein at least part of the lumen is within a tube separate from the housing.

23. The apparatus of claim 21, wherein the lumen opens into the chamber at a location not faced by the transducer.

24. The apparatus of claim 16, wherein the exhaust port comprises a valve fixed with respect to the wall.

25. The apparatus of claim 24, wherein the valve is placed in the wall at a location not faced by the transducer.

26. The apparatus of claim 16, further comprising a motor operatively connected to the transducer, and a seal between the motor and the transducer and fixed to the wall, the seal defining a rearward boundary of the chamber.

27. The apparatus of claim 26, wherein the injection port is located opposite and facing the seal.

28. The apparatus of claim 26, wherein the injection port is located adjacent the seal.

29. The apparatus of claim 26, wherein the exhaust port is located adjacent the seal.

30. The apparatus of claim 26, wherein the injection port and the exhaust port are located diametrically opposed from each other.

31. A method of preparing a device for ultrasound procedures, comprising:
injecting a coupling medium into a sealed chamber, the chamber defined at least partially by a wall forming an acoustic window for transmission of ultrasound signals, the chamber having within it a transducer for emitting and/or receiving ultrasound signals, the chamber having an exhaust port extending through the wall forming an acoustic window and in fluid communication with the chamber through which gas within the chamber can be evacuated, and
wherein the injecting includes moving the coupling medium through an injection port extending through the wall forming an acoustic window that communicates with the chamber, and wherein the injecting includes passing the coupling medium through a lumen in a tube, at least part of the tube being within a housing of the device.

32. The method of claim 31, wherein during the injecting, gas within the chamber prior to the injecting is forced out of the chamber through the exhaust port.

33. The method of claim 31, including evacuating gas through the exhaust port from within the chamber prior to injecting medium into the chamber.

34. The method of claim 31, wherein the injecting continues until the coupling medium displaces substantially all of the gas.

35. The method of claim 31, wherein the injecting includes inserting a needle through the injection port and passing the coupling medium through the needle and into the chamber.

36. The method of claim 31, wherein the exhaust port includes a valve, so that during the injecting, gas within the chamber prior to the injecting is forced out of the chamber and exterior of the device through the valve.

37. A method of preparing a device for ultrasound procedures, comprising:
injecting a coupling medium into a sealed chamber, the chamber defined at least partially by a wall forming an acoustic window for transmission of ultrasound signals, the chamber having within it a transducer for emitting and/or receiving ultrasound signals, the chamber having an exhaust port extending through the wall forming an acoustic window and in fluid communication with the chamber through which gas within the chamber can be evacuated, and
wherein the injecting includes moving the coupling medium through an injection port extending through the wall forming an acoustic window that communicates with the chamber, wherein the exhaust port includes a lumen in a tube, at least part of the tube being within a housing of the device, wherein during the injecting, gas within the chamber prior to the injecting is forced out of the chamber through at least part of the lumen.

38. The method of claim 37, wherein the injecting includes passing the coupling medium through the lumen in the tube, at least part of the tube being within the housing of the device.

39. The method of claim 37, wherein the exhaust port includes a valve, so that during the injecting, gas within the chamber prior to the injecting is forced out of the chamber and exterior of the device through the valve.

* * * * *